United States Patent
Saboe et al.

(10) Patent No.: US 11,279,666 B2
(45) Date of Patent: Mar. 22, 2022

(54) ADVANCED ADSORPTION PROCESSES FOR SEPARATION OF BIO-DERIVED PRODUCTS

(71) Applicant: Alliance for Sustainable Energy, LLC, Golden, CO (US)

(72) Inventors: Patrick Owen Saboe, Golden, CO (US); Eric M. Karp, Denver, CO (US); Lorenz Perry Manker, Jamaica Plain, MA (US); Hanna Rose Monroe, Broomfield, CO (US)

(73) Assignee: Alliance for Sustainable Energy, LLC, Golden, CO (US)

( * ) Notice: Subject to any disclaimer, the term of this patent is extended or adjusted under 35 U.S.C. 154(b) by 0 days.

(21) Appl. No.: 16/942,888

(22) Filed: Jul. 30, 2020

(65) Prior Publication Data

US 2021/0032188 A1    Feb. 4, 2021

Related U.S. Application Data

(60) Provisional application No. 62/880,395, filed on Jul. 30, 2019.

(51) Int. Cl.

| | |
|---|---|
| *C07C 51/47* | (2006.01) |
| *B01J 20/26* | (2006.01) |
| *B01J 20/34* | (2006.01) |
| *B01D 3/40* | (2006.01) |
| *C07C 51/44* | (2006.01) |
| *B01D 17/02* | (2006.01) |
| *B01D 3/14* | (2006.01) |
| *C12M 1/00* | (2006.01) |

(52) U.S. Cl.
CPC .............. *C07C 51/47* (2013.01); *B01D 3/143* (2013.01); *B01D 3/40* (2013.01); *B01D 17/0202* (2013.01); *B01J 20/261* (2013.01); *B01J 20/3425* (2013.01); *B01J 20/3475* (2013.01); *C07C 51/44* (2013.01); *C12M 47/10* (2013.01)

(58) Field of Classification Search
CPC ....... C07C 51/47; C07C 51/44; C07C 53/124; B01D 3/143; B01D 3/40; B01D 17/0202; B01D 3/002; B01J 20/261; B01J 20/3475; B01J 20/3425; B01J 41/07; C12M 47/10
See application file for complete search history.

(56) References Cited

U.S. PATENT DOCUMENTS

| | | | |
|---|---|---|---|
| 4,323,702 A | 4/1982 | Kawabata et al. | |
| 5,068,419 A | 11/1991 | Kulprathipanja et al. | |
| 5,412,126 A | 5/1995 | King et al. | |
| 5,965,771 A * | 10/1999 | King | C07C 51/47 |
| | | | 562/580 |
| 6,316,668 B1 * | 11/2001 | King | C07C 51/47 |
| | | | 554/184 |

OTHER PUBLICATIONS

Richter et al. (A Narrow pH Range Supports Butanol, Hexanol, and Octanol Production from Syngas in a Continuous Co-culture of Clostridium Ijungdahlii and Clostridium kluyveri with In-Line Product Extraction, Frontiers in microbiology, 7, pp. 1-13, Published 2016) (Year: 2016).*

Delgado et al. "Modeling of the separation of lactic acid from an aqueous mixture by adsorption on polyvinylpyridine resin and desorption with methanol", Separation and Purification Technology, Jul. 2018, vol. 200, pp. 307-317.

Husson et al., "Regeneration of lactic and succinic acid-laden basic sorbents by leaching with a volatile base in an organic solvent", Industrial & Engineering Chemistry Research, Apr. 1998, vol. 37, No. 8, pp. 2996-3005.

Saboe et al., "In situ recovery of bio-based carboxylic acids", Green Chemistry, 2018, vol. 20, No. 8, pp. 1791-1804.

* cited by examiner

*Primary Examiner* — Yevgeny Valenrod
*Assistant Examiner* — Blaine G Doletski
(74) *Attorney, Agent, or Firm* — Sam J. Barkley

(57) ABSTRACT

Disclosed herein are methods for the recovery of target bio-base carboxylic acid products using a sorption-based technology with a mixed elution solvent optimized for minimized downstream distillation energy input. The sorption-based technology includes absorbing the targeted bio-base carboxylic acid products onto a non-ionic resin and eluting the targeted bio-base carboxylic acid products with a mixed elution solvent. The mixed elution solvent includes a first solvent and a second solvent. The first solvent has a boiling point that is lower than the targeted bio-base carboxylic acid products and the second solvent is selected from the group consisting of a phosphine oxide or tertiary amine.

14 Claims, No Drawings

ADVANCED ADSORPTION PROCESSES FOR SEPARATION OF BIO-DERIVED PRODUCTS

CROSS-REFERENCE TO RELATED APPLICATIONS

This application claims priority under 35 U.S.C. § 119 to U.S. provisional patent application No. 62/880,395 filed on 30 Jul. 2019, the contents of which are hereby incorporated in their entirety.

CONTRACTUAL ORIGIN

The United States Government has rights in this invention under Contract No. DE-AC36-08GO28308 between the United States Department of Energy and the Alliance for Sustainable Energy, LLC, the Manager and Operator of the National Renewable Energy Laboratory.

BACKGROUND

Current sorption-based technologies are generally cost intensive and environmentally burdensome because of the costs associated with the required strong acid, as well as the inherent costs of other required materials and the energy input needed to separate the elution solvent from the target product. Furthermore, current sorption technologies using non-ionic resins for carboxylic acids require large volumes of solvent, and complex, energy and material intensive processes to ensure high product and solvent recovery.

SUMMARY

In an aspect, disclosed herein is a method for separating a bio-based product from an aqueous solution. In an embodiment, the bio-based product is an alcohol. In an embodiment, the bio-based product is a carboxylic acid. In an embodiment, the carboxylic acid is lactic acid or butyric acid. In an embodiment, the method further comprises the step of selecting a first solvent and a second solvent wherein the first solvent has a boiling point that is lower than the bio-based product and wherein the second solvent is miscible with the first solvent and has a boiling point above the bio-based product. In an embodiment, the first solvent is selected from the group consisting of acetone and methanol. In an embodiment, the second solvent is selected from the group consisting of a phosphine oxide or tertiary amine. In an embodiment, the adsorption of the bio-based product onto a non-ionic resin. In an embodiment, the non-ionic resin is selected from the group consisting of Amberlite™, Dowex®, or Polybenzimidazole (PBI). In an embodiment, the non-ionic resin is poly(4-vinylpyridine). In an embodiment, the method further comprises desorbing the bio-based product from the resin using a mixture of the first solvent and the second solvent. In an embodiment, the method further comprises distilling the first and second solvent from a mixture of the desorbed bio-based product and the first and second solvent. In an embodiment, the bio-based product is isolated.

In another aspect, disclosed herein is a method for separating a fermentation product from an aqueous solution comprising adsorption of the fermentation product onto a non-ionic resin and further comprising the step of selecting a first solvent and a second solvent wherein the first solvent has a boiling point that is lower than the fermentation product and wherein the second solvent is miscible with the first solvent and has a boiling point above the fermentation product. In an embodiment, the fermentation product is selected from the group consisting of alcohols and carboxylic acids. In an embodiment, the first solvent is selected from the group consisting of acetone and methanol and wherein the second solvent is selected from the group consisting of a phosphine oxide or tertiary amine. In an embodiment, the non-ionic resin is poly(4-vinylpyridine). In an embodiment, the method further comprises desorbing the fermentation product from the resin using a mixture of the first solvent and the second solvent. In an embodiment, the method further comprises distilling the first and second solvent from a mixture of the desorbed fermentation product and the first and second solvent. In an embodiment, the fermentation product is isolated.

Other objects, advantages, and novel features of the present invention will become apparent from the following detailed description of the invention when considered in conjunction with the accompanying drawings.

DESCRIPTION OF THE DRAWINGS

None.

DETAILED DESCRIPTION

Disclosed herein are systems and methods useful for optimizing the recovery of target bio-based products using a sorption-based technology with a mixed elution solvent optimized for minimized downstream distillation energy input.

Separations of bio-derived products from fermentation broth is expensive and has impeded the adoption of advanced bioprocessing of renewable chemicals. The processes disclosed herein are useful for increased efficient recovery of bio-based products using a sorption-based technology with a mixed elution solvent optimized for minimized downstream distillation energy input.

In an embodiment, disclosed herein are processes wherein a bio-based product, the target product, such as a carboxylic acid or alcohol, are purified from fermentation broth or any dilute aqueous feed stream (such as waste water, for example). As disclosed herein, the process can implement any non-ionic resin, for example, poly(4-vinylpyridine) (PVP), to absorb a target product. The adsorbed target product, retained on the resin, is then desorbed using a solvent mixture containing two solvents which are mixed together to form an elution solvent. A first solvent has a boiling point that is lower than the target product and is miscible with water, for example, acetone and methanol. A second solvent contains a phosphine oxide or tertiary amine molecule that is miscible with the first solvent and has a boiling point above the target product.

In an embodiment, elution solvents used may include aliphatic alcohols such as methanol, ethanol, and propanol; aliphatic ketones such as acetone, and methyl ethyl ketone; as well as esters such as methyl acetate, ethyl acetate, and methyl propionate. In an embodiment, a first solvent includes aliphatic alcohols such as methanol, ethanol, and propanol; aliphatic ketones such as acetone, and methyl ethyl ketone; as well as esters such as methyl acetate, ethyl acetate, and methyl propionate. In an embodiment, a high molecular weight amine is used as part of an elution solvent.

In an embodiment, a distillation process to recover volatile fatty acids (VFAs) from a non-volatile extractant such as Cyanex 923 and tri-octylamine.

In an embodiment, the elution solvent is loaded with a desorbed target product and is then separated from the target product in a thermally driven distillation process. Solvent one and two are then recovered after the distillation process and are mixed together to form a recycle elution solvent loop. In an embodiment, the target product is recovered using the distillation process or may be used as a reactant within a reactive distillation unit.

In an embodiment, the processes disclosed herein are used to separate bio-based products (the target product) such as carboxylic acids and alcohols from dilute aqueous feed streams such as a fermentation broth. The target product is recovered within the distillation process or used as a reactant within a reactive distillation unit. The processes disclosed herein are a significant economic improvement over existing product separations including separation of bio-derived lactic acid.

In an embodiment, a volatile alkylamine base is used to desorb carboxylic acids from weak base resins and a distillation process is used to recover the volatile base and carboxylic acid. In an embodiment an elution solvent is used that is appropriate for recovery of lactic acid from weak base resins. In another embodiment, an elution solvent containing a volatile amine mixed with acetonitrile for the use of desorbing lactic acid from a weak base resin is disclosed herein. The lactic acid is then recovered from the elution solvent by evaporating the volatile amine in a water free system. In an embodiment, a weak-base resin may be used as a part of the separation processes disclosed herein. In another embodiment, the elution solvent may contain methanol and use of non-ionic resins including polyvinylpyridine.

A Freundlich isotherm model describes equilibrium data of butyric acid adsorption using the various solvents.

$$q = \frac{1}{K_R}(C_{EQ})^{1/n} \quad (1)$$

In equation 1, q is the uptake of acid onto the resin (g acid/g dry resin), $C_{EQ}$ is the equilibrium concentration of acid remaining in the solvent after uptake (g/L), $K_R$ is the regeneration constant that is proportional to the affinity of the solvent for the acid, and 1/n is a constant that indicates the linearity of the isotherm.

EXAMPLES

Adsorption isotherms for butyric acid onto for four resins were conducted in several solvents. The general trend of increasing regeneration constant is Cyanex 923>DMSO>methanol>acetone. 1/n values for Cyanex 923 are greater than 1, which is indicative of cooperative adsorption of butyric acid. High regeneration constants are ideal for elution solvents. Table 1 depicts a comparison of elution solvents for butyric acid recovery from weak base resins.

TABLE 1

Freundlich K-parameter of solvent-resin mixtures

| Resin | Water | Acetone | Methanol | DMSO | Cyanex |
|---|---|---|---|---|---|
| Amberlite ™ IRA-96 | 3.80 | 7.60 | 13.1 | 26.0 | 4490 |
| Dowex ® 77 | 4.10 | 11.4 | 18.7 | 101 | 10000 |
| Polybenzimidazole | 13.2 | 15.8 | 205 | n/a | 2790 |
| Reillex 425 (PVP) | 20.5 | 23.0 | 671 | 330 | 8580 |

In an embodiment, an elution solvent consisting of 90% acetone as a first solvent and 10% cyanex as a second solvent was used to elute adsorbed butyric acid (a bio-based product) from a PVP resin.

In an embodiment, an elution curve was generated with using butyric acid with PVP (Reillex Y25) resin and a 90/10 acetone/cyanex elution solvent solution to determine the volume of 90% acetone/10% cyanex needed to recover 100% of the butyric acid.

The elution experiment used 5.03 grams of PVP resin inside of a column having a mass of 306.57 g for a combined weight of resin and column of 326.245 g. The bed volume was 14 mL. The tare weight of the effluent bottle was measured at 141.67 g. The uptake calculated by theory is 0.0616 g acid per gram of dry resin. The theoretical effluent amount is 15.62 g in 22.32 min at 0.7 mL per min. The actual effluent amount was measured at 15.63 g. Fractions of effluent were collected as they ran off the column and had the following characteristics as listed in Table 2.

TABLE 2

Properties of effluent fractions.

| Tube # | Tare tube (g) | Mass fraction + tube (g) | Density fraction (g/mL) | Water conc. (wt %) |
|---|---|---|---|---|
| 1 | 5.4393 | 7.6634 | 0.9982 | 97.74 |
| 2 | 5.4815 | 7.2760 | 0.9993 | 113.19 |
| 3 | 5.5224 | 8.1462 | 0.9981 | 109.17 |
| 4 | 5.3844 | 6.8664 | 0.9988 | 92.36 |
| 5 | 5.3751 | 7.3096 | 0.9971 | 106.25 |
| 6 | 5.3655 | 8.0787 | | |
| 7 | 5.4369 | 7.6119 | | |
| 8 | 5.4371 | 7.2322 | | |
| 9 | 5.3799 | 7.0879 | 0.8687 | 27.82, 26.84 |
| 10 | 5.4725 | 7.1179 | 0.8494 | 18.05 |
| 11 | 5.3753 | 7.1365 | 0.8441 | 18.98 |
| 12 | 5.4050 | 7.1136 | 0.8299 | 12.55 |

The foregoing disclosure has been set forth merely to illustrate the invention and is not intended to be limiting.

We claim:

1. A method for separating a bio-based carboxylic acid product from an aqueous solution comprising the step of selecting a first solvent and a second solvent wherein the first solvent has a boiling point that is lower than the bio-based carboxylic acid product and wherein the second solvent is selected from the group consisting of a phosphine oxide or tertiary amine and is miscible with the first solvent and has a boiling point above the bio-based carboxylic acid product; and further comprising the adsorption of the bio-based carboxylic acid product onto a non-ionic resin.

2. The method of claim 1 wherein the carboxylic acid is lactic acid or butyric acid.

3. The method of claim 1 wherein the first solvent is selected from the group consisting of acetone and methanol.

4. The method of claim 1 wherein the non-ionic resin is selected from the group consisting of Amberlite™, Dowex®, or Polybenzimidazole (PBI).

5. The method of claim 1 wherein the non-ionic resin is poly(4-vinylpyridine).

6. The method of claim 1 wherein the method further comprises desorbing the bio-based carboxylic acid product from the resin using a mixture of the first solvent and the second solvent.

7. The method of claim 6 further comprising distilling the first and second solvent from a mixture of the desorbed bio-based carboxylic acid product and the first and second solvent.

8. The method of claim 7 wherein the bio-based product is isolated.

9. A method for separating a carboxylic acid fermentation product from an aqueous solution comprising adsorption of the carboxylic acid fermentation product onto a non-ionic resin and further comprising the step of selecting a first solvent and a second solvent wherein the second solvent is selected from the group consisting of a phosphine oxide or tertiary amine and wherein the first solvent has a boiling point that is lower than the carboxylic acid fermentation product and wherein the second solvent is miscible with the first solvent and has a boiling point above the carboxylic acid fermentation product.

10. The method of claim 9 wherein the first solvent is selected from the group consisting of acetone and methanol.

11. The method of claim 9 wherein the non-ionic resin is poly(4-vinylpyridine).

12. The method of claim 9 wherein the method further comprises desorbing the fermentation product from the resin using a mixture of the first solvent and the second solvent.

13. The method of claim 12 further comprising distilling the first and second solvent from a mixture of the desorbed carboxylic acid fermentation product and the first and second solvent.

14. The method of claim 13 wherein the carboxylic acid fermentation product is isolated.

\* \* \* \* \*